(12) United States Patent
Meridew et al.

(10) Patent No.: US 8,900,244 B2
(45) Date of Patent: Dec. 2, 2014

(54) PATIENT-SPECIFIC ACETABULAR GUIDE AND METHOD

(75) Inventors: Jason D. Meridew, Warsaw, IN (US); Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 352 days.

(21) Appl. No.: 13/343,957

(22) Filed: Jan. 5, 2012

(65) Prior Publication Data

US 2012/0109138 A1 May 3, 2012

Related U.S. Application Data

(60) Division of application No. 12/389,901, filed on Feb. 20, 2009, now Pat. No. 8,133,234, which is a (Continued)

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61F 2/30* | (2006.01) |
| *A61B 17/22* | (2006.01) |
| *A61B 19/00* | (2006.01) |

(52) U.S. Cl.
CPC ....... *A61F 2/4609* (2013.01); *A61F 2002/4662* (2013.01); *A61F 2/30942* (2013.01); *A61B 2017/22001* (2013.01); *A61F 2002/4668* (2013.01); *A61F 2002/30617* (2013.01); *A61F 2002/4687* (2013.01); *A61B 19/50* (2013.01); *A61F 2250/0097* (2013.01); *A61F 2/00* (2013.01)
USPC .......................................... 606/91

(58) Field of Classification Search
CPC . A61F 2/00; A61F 2/4609; A61F 2002/4662; A61F 2002/4681; A61F 2002/4687
USPC ................ 623/21.18–22.21, 18.11–20.11, 623/22.22–22.4; 606/91–93, 99, 86 R, 606/79–81
See application file for complete search history.

(56) References Cited

U.S. PATENT DOCUMENTS

| | | | |
|---|---|---|---|
| 1,480,285 | A | 1/1924 | Moore |
| 2,181,746 | A | 11/1939 | Siebrandt |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

International Preliminary Report on Patentability mailed Sep. 6, 2013 for PCT/US2012/026356 claiming benefit of U.S. Appl. No. 13/041,883, filed Mar. 7, 2011.

(Continued)

*Primary Examiner* — Alvin Stewart
(74) *Attorney, Agent, or Firm* — Harness, Dickey

(57) ABSTRACT

A method for inserting an acetabular cup into an acetabulum of a patient includes inspecting a preoperative plan including a three-dimensional image of a patient's acetabulum, selecting at least one of a patient-specific anteversion angle and a patient-specific abduction angle, and approving the preoperative plan. The method also includes preparing the patient's acetabulum for implantation, positioning a patient-specific first surface of an acetabular guide around a matched acetabular rim surface of the patient, and inserting an acetabular cup through an opening of the acetabular guide, the opening having a cylindrical inner surface oriented at the selected at least one of the patient-specific anteversion angle and patient-specific abduction angle.

16 Claims, 4 Drawing Sheets

Related U.S. Application Data continuation-in-part of application No. 11/756,057, filed on May 31, 2007, now Pat. No. 8,092,465, and a continuation-in-part of application No. 12/211,407, filed on Sep. 16, 2008, now Pat. No. 8,608,748, which is a continuation-in-part of application No. 11/971,390, filed on Jan. 9, 2008, now Pat. No. 8,070,752, which is a continuation-in-part of application No. 11/363,548, filed on Feb. 27, 2006, now Pat. No. 7,780,672.

(60) Provisional application No. 60/812,694, filed on Jun. 9, 2006.

(56) References Cited

U.S. PATENT DOCUMENTS

| | | | |
|---|---|---|---|
| 2,407,845 | A | 9/1946 | Nemeyer |
| 2,416,228 | A | 2/1947 | Sheppard |
| 2,618,913 | A | 11/1952 | Plancon et al. |
| 2,910,978 | A | 11/1959 | Urist |
| 3,840,904 | A | 10/1974 | Tronzo |
| 4,246,895 | A | 1/1981 | Rehder |
| 4,306,866 | A | 12/1981 | Weissman |
| 4,324,006 | A | 4/1982 | Charnley |
| 4,421,112 | A | 12/1983 | Mains et al. |
| 4,436,684 | A | 3/1984 | White |
| 4,457,306 | A | 7/1984 | Borzone |
| 4,475,549 | A | 10/1984 | Oh |
| 4,506,393 | A | 3/1985 | Murphy |
| 4,524,766 | A | 6/1985 | Petersen |
| 4,528,980 | A * | 7/1985 | Kenna ............................... 606/80 |
| 4,619,658 | A | 10/1986 | Pappas et al. |
| 4,621,630 | A | 11/1986 | Kenna |
| 4,632,111 | A | 12/1986 | Roche |
| 4,633,862 | A | 1/1987 | Petersen |
| 4,663,720 | A | 5/1987 | Duret et al. |
| 4,689,984 | A | 9/1987 | Kellner |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,706,660 | A | 11/1987 | Petersen |
| 4,719,907 | A | 1/1988 | Banko et al. |
| 4,721,104 | A | 1/1988 | Kaufman et al. |
| 4,722,330 | A | 2/1988 | Russell et al. |
| 4,759,350 | A | 7/1988 | Dunn et al. |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A | 1/1990 | Vandewalls |
| 4,907,577 | A | 3/1990 | Wu |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A * | 4/1991 | Woolson ....................... 128/898 |
| 5,030,221 | A | 7/1991 | Buechel et al. |
| 5,041,117 | A | 8/1991 | Engelhardt |
| 5,053,037 | A | 10/1991 | Lackey |
| 5,053,039 | A | 10/1991 | Hofmann et al. |
| 5,056,351 | A | 10/1991 | Stiver et al. |
| 5,086,401 | A * | 2/1992 | Glassman et al. ............. 700/259 |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A | 6/1992 | Bert et al. |
| 5,123,927 | A * | 6/1992 | Duncan et al. ............. 623/20.21 |
| 5,129,908 | A | 7/1992 | Petersen |
| 5,129,909 | A | 7/1992 | Sutherland |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,194,066 | A | 3/1993 | Van Zile |
| 5,234,433 | A | 8/1993 | Bert et al. |
| 5,246,444 | A | 9/1993 | Schreiber |
| 5,253,506 | A | 10/1993 | Davis et al. |
| 5,258,032 | A | 11/1993 | Bertin |
| 5,261,915 | A | 11/1993 | Durlacher et al. |
| 5,274,565 | A * | 12/1993 | Reuben ........................ 700/182 |
| 5,299,288 | A * | 3/1994 | Glassman et al. ............. 700/245 |
| 5,300,077 | A | 4/1994 | Howell |
| 5,320,529 | A | 6/1994 | Pompa |
| 5,320,625 | A * | 6/1994 | Bertin .............................. 606/91 |
| 5,323,697 | A | 6/1994 | Schrock |
| 5,342,366 | A | 8/1994 | Whiteside et al. |
| 5,344,423 | A | 9/1994 | Dietz et al. |
| 5,360,446 | A | 11/1994 | Kennedy |
| 5,364,402 | A | 11/1994 | Mumme et al. |
| 5,368,858 | A | 11/1994 | Hunziker |
| 5,370,692 | A * | 12/1994 | Fink et al. ..................... 128/898 |
| 5,370,699 | A | 12/1994 | Hood et al. |
| 5,405,395 | A | 4/1995 | Coates |
| 5,408,409 | A | 4/1995 | Glassman et al. |
| 5,411,521 | A | 5/1995 | Putnam et al. |
| 5,415,662 | A | 5/1995 | Ferrante et al. |
| 5,417,694 | A | 5/1995 | Marik et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |
| 5,462,550 | A | 10/1995 | Dietz et al. |
| 5,472,415 | A | 12/1995 | King et al. |
| 5,474,559 | A | 12/1995 | Bertin et al. |
| 5,490,854 | A | 2/1996 | Fisher et al. |
| 5,496,324 | A | 3/1996 | Barnes |
| 5,507,833 | A | 4/1996 | Bohn |
| 5,514,519 | A | 5/1996 | Neckers |
| 5,520,695 | A | 5/1996 | Luckman |
| 5,527,317 | A * | 6/1996 | Ashby et al. .................... 606/91 |
| 5,539,649 | A | 7/1996 | Walsh et al. |
| 5,540,695 | A | 7/1996 | Levy |
| 5,545,222 | A | 8/1996 | Bonutti |
| 5,549,688 | A | 8/1996 | Ries et al. |
| 5,554,190 | A | 9/1996 | Draenert |
| 5,560,096 | A | 10/1996 | Stephens |
| 5,571,110 | A | 11/1996 | Matsen, III et al. |
| 5,578,037 | A | 11/1996 | Sanders et al. |
| 5,593,411 | A | 1/1997 | Stalcup et al. |
| 5,595,703 | A | 1/1997 | Swaelens et al. |
| 5,607,431 | A | 3/1997 | Dudasik et al. |
| 5,611,802 | A | 3/1997 | Samuelson et al. |
| 5,613,969 | A | 3/1997 | Jenkins, Jr. |
| 5,620,448 | A | 4/1997 | Puddu |
| 5,634,927 | A | 6/1997 | Houston et al. |
| 5,641,323 | A | 6/1997 | Caldarise |
| 5,653,714 | A | 8/1997 | Dietz et al. |
| 5,658,294 | A | 8/1997 | Sederholm |
| 5,662,656 | A | 9/1997 | White |
| 5,662,710 | A | 9/1997 | Bonutti |
| 5,671,018 | A | 9/1997 | Ohara et al. |
| 5,676,668 | A | 10/1997 | McCue et al. |
| 5,677,107 | A | 10/1997 | Neckers |
| 5,681,354 | A | 10/1997 | Eckhoff |
| 5,682,886 | A | 11/1997 | Delp et al. |
| 5,683,469 | A | 11/1997 | Johnson et al. |
| 5,690,635 | A | 11/1997 | Matsen, III et al. |
| 5,697,933 | A | 12/1997 | Gundlapalli et al. |
| 5,702,460 | A | 12/1997 | Carls et al. |
| 5,702,464 | A | 12/1997 | Lackey et al. |
| 5,704,941 | A | 1/1998 | Jacober et al. |
| 5,709,689 | A | 1/1998 | Ferrante et al. |

(56) References Cited

U.S. PATENT DOCUMENTS

| | | | |
|---|---|---|---|
| 5,720,752 A | 2/1998 | Elliott et al. | |
| 5,722,978 A | 3/1998 | Jenkins, Jr. | |
| 5,725,376 A | 3/1998 | Poirier | |
| 5,725,593 A | 3/1998 | Caracciolo | |
| 5,735,277 A | 4/1998 | Schuster | |
| 5,748,767 A | 5/1998 | Raab | |
| 5,749,875 A | 5/1998 | Puddu | |
| 5,749,876 A | 5/1998 | Duvillier et al. | |
| 5,762,125 A | 6/1998 | Mastrorio | |
| 5,768,134 A * | 6/1998 | Swaelens et al. | 700/121 |
| 5,769,092 A * | 6/1998 | Williamson, Jr. | 128/898 |
| 5,776,200 A | 7/1998 | Johnson et al. | |
| 5,786,217 A | 7/1998 | Tubo et al. | |
| 5,792,143 A | 8/1998 | Samuelson et al. | |
| 5,798,924 A * | 8/1998 | Eufinger et al. | 700/117 |
| 5,799,055 A | 8/1998 | Peshkin et al. | |
| 5,835,619 A | 11/1998 | Morimoto et al. | |
| 5,860,980 A | 1/1999 | Axelson, Jr. | |
| 5,860,981 A | 1/1999 | Bertin et al. | |
| 5,871,018 A * | 2/1999 | Delp et al. | 128/898 |
| 5,876,456 A | 3/1999 | Sederholm et al. | |
| 5,879,398 A | 3/1999 | Swarts et al. | |
| 5,879,402 A | 3/1999 | Lawes et al. | |
| 5,880,976 A | 3/1999 | DiGioia, III et al. | |
| 5,885,297 A | 3/1999 | Matsen, III | |
| 5,885,298 A | 3/1999 | Herrington et al. | |
| 5,888,219 A | 3/1999 | Bonutti | |
| 5,895,389 A | 4/1999 | Schenk et al. | |
| 5,899,907 A | 5/1999 | Johnson | |
| 5,901,060 A | 5/1999 | Schall et al. | |
| 5,911,724 A | 6/1999 | Wehrli | |
| 5,921,988 A | 7/1999 | Legrand | |
| 5,925,049 A | 7/1999 | Gustilo et al. | |
| 5,942,370 A | 8/1999 | Neckers | |
| 5,967,777 A | 10/1999 | Klein et al. | |
| 5,976,149 A | 11/1999 | Masini | |
| 5,980,526 A | 11/1999 | Johnson et al. | |
| 6,033,415 A | 3/2000 | Mittelstadt et al. | |
| 6,056,754 A | 5/2000 | Haines et al. | |
| 6,059,789 A | 5/2000 | Dinger et al. | |
| 6,059,833 A | 5/2000 | Doets | |
| 6,086,593 A | 7/2000 | Bonutti | |
| 6,120,510 A | 9/2000 | Albrektsson et al. | |
| 6,120,544 A | 9/2000 | Grundei et al. | |
| 6,126,690 A | 10/2000 | Ateshian et al. | |
| 6,126,692 A | 10/2000 | Robie et al. | |
| 6,136,033 A | 10/2000 | Suemer | |
| 6,156,069 A | 12/2000 | Amstutz | |
| 6,159,217 A | 12/2000 | Robie et al. | |
| 6,161,080 A * | 12/2000 | Aouni-Ateshian et al. | 703/11 |
| 6,162,257 A | 12/2000 | Gustilo et al. | |
| 6,187,010 B1 | 2/2001 | Masini | |
| 6,195,615 B1 | 2/2001 | Lysen | |
| 6,203,546 B1 | 3/2001 | MacMahon | |
| 6,205,411 B1 * | 3/2001 | DiGioia et al. | 703/11 |
| 6,206,927 B1 | 3/2001 | Fell et al. | |
| 6,210,445 B1 | 4/2001 | Zawadzki | |
| 6,238,435 B1 | 5/2001 | Meulink et al. | |
| 6,254,604 B1 | 7/2001 | Howell | |
| 6,258,097 B1 | 7/2001 | Cook et al. | |
| 6,264,698 B1 | 7/2001 | Lawes et al. | |
| 6,270,529 B1 | 8/2001 | Terrill-Grisoni et al. | |
| 6,273,891 B1 | 8/2001 | Masini | |
| 6,290,727 B1 | 9/2001 | Otto et al. | |
| 6,293,971 B1 | 9/2001 | Nelson et al. | |
| 6,310,269 B1 | 10/2001 | Friese et al. | |
| 6,312,258 B1 | 11/2001 | Ashman | |
| 6,312,473 B1 | 11/2001 | Oshida | |
| 6,319,285 B1 | 11/2001 | Chamier et al. | |
| 6,325,829 B1 | 12/2001 | Schmotzer | |
| 6,338,738 B1 | 1/2002 | Bellotti et al. | |
| 6,343,987 B2 | 2/2002 | Hayama et al. | |
| 6,354,011 B1 | 3/2002 | Albrecht | |
| 6,361,563 B2 | 3/2002 | Terrill-Grisoni et al. | |
| 6,379,299 B1 | 4/2002 | Borodulin et al. | |
| 6,379,388 B1 | 4/2002 | Ensign et al. | |
| 6,383,228 B1 | 5/2002 | Schmotzer | |
| 6,391,251 B1 | 5/2002 | Keicher et al. | |
| 6,395,005 B1 | 5/2002 | Lovell | |
| 6,424,332 B1 | 7/2002 | Powell | |
| 6,427,698 B1 | 8/2002 | Yoon | |
| 6,459,948 B1 | 10/2002 | Ateshian et al. | |
| 6,463,351 B1 | 10/2002 | Clynch | |
| 6,475,243 B1 | 11/2002 | Sheldon et al. | |
| 6,482,236 B2 | 11/2002 | Habecker | |
| 6,488,715 B1 | 12/2002 | Pope et al. | |
| 6,503,255 B1 | 1/2003 | Albrektsson et al. | |
| 6,510,334 B1 | 1/2003 | Schuster et al. | |
| 6,514,259 B2 | 2/2003 | Picard et al. | |
| 6,517,583 B1 | 2/2003 | Pope et al. | |
| 6,519,998 B2 | 2/2003 | Ertl et al. | |
| 6,520,964 B2 | 2/2003 | Tallarida et al. | |
| 6,533,737 B1 | 3/2003 | Brosseau et al. | |
| 6,547,823 B2 | 4/2003 | Scarborough et al. | |
| 6,554,837 B1 | 4/2003 | Hauri et al. | |
| 6,556,008 B2 | 4/2003 | Thesen | |
| 6,558,391 B2 | 5/2003 | Axelson, Jr. et al. | |
| 6,558,428 B2 | 5/2003 | Park | |
| 6,564,085 B2 | 5/2003 | Meaney et al. | |
| 6,567,681 B1 | 5/2003 | Lindequist | |
| 6,575,980 B1 | 6/2003 | Robie et al. | |
| 6,575,982 B1 | 6/2003 | Bonutti | |
| 6,591,581 B2 | 7/2003 | Schmieding | |
| 6,605,293 B1 | 8/2003 | Giordano et al. | |
| 6,622,567 B1 | 9/2003 | Hamel et al. | |
| 6,629,999 B1 | 10/2003 | Serafin, Jr. | |
| 6,641,617 B1 | 11/2003 | Merrill et al. | |
| 6,682,566 B2 | 1/2004 | Draenert | |
| 6,696,073 B2 | 2/2004 | Boyce et al. | |
| 6,697,664 B2 | 2/2004 | Kienzle, III et al. | |
| 6,701,174 B1 | 3/2004 | Krause et al. | |
| 6,709,462 B2 | 3/2004 | Hanssen | |
| 6,711,431 B2 | 3/2004 | Sarin et al. | |
| 6,711,432 B1 | 3/2004 | Krause et al. | |
| 6,712,856 B1 * | 3/2004 | Carignan et al. | 623/20.35 |
| 6,716,249 B2 | 4/2004 | Hyde | |
| 6,725,077 B1 | 4/2004 | Balloni et al. | |
| 6,738,657 B1 | 5/2004 | Franklin et al. | |
| 6,740,092 B2 | 5/2004 | Lombardo et al. | |
| 6,749,638 B1 | 6/2004 | Saladino | |
| 6,750,653 B1 | 6/2004 | Zou et al. | |
| 6,772,026 B2 * | 8/2004 | Bradbury et al. | 700/98 |
| 6,780,190 B2 | 8/2004 | Maroney | |
| 6,786,930 B2 | 9/2004 | Biscup | |
| 6,799,066 B2 | 9/2004 | Steines et al. | |
| 6,823,871 B2 | 11/2004 | Schmieding | |
| 6,827,723 B2 | 12/2004 | Carson | |
| 6,887,247 B1 | 5/2005 | Couture et al. | |
| 6,905,514 B2 * | 6/2005 | Carignan et al. | 623/20.35 |
| 6,923,817 B2 | 8/2005 | Carson et al. | |
| 6,923,831 B2 | 8/2005 | Fell et al. | |
| 6,932,842 B1 * | 8/2005 | Litschko et al. | 623/16.11 |
| 6,942,475 B2 | 9/2005 | Ensign et al. | |
| 6,944,518 B2 * | 9/2005 | Roose | 700/117 |
| 6,945,976 B2 | 9/2005 | Ball et al. | |
| 6,953,480 B2 | 10/2005 | Mears et al. | |
| 6,960,216 B2 | 11/2005 | Kolb et al. | |
| 6,975,755 B1 * | 12/2005 | Baumberg | 382/154 |
| 6,990,220 B2 | 1/2006 | Ellis et al. | |
| 7,029,479 B2 | 4/2006 | Tallarida et al. | |
| 7,042,222 B2 | 5/2006 | Zheng et al. | |
| 7,048,741 B2 | 5/2006 | Swanson | |
| 7,050,877 B2 | 5/2006 | Iseki et al. | |
| 7,060,074 B2 | 6/2006 | Rosa et al. | |
| 7,074,241 B2 | 7/2006 | McKinnon | |
| RE39,301 E | 9/2006 | Bertin | |
| 7,104,997 B2 | 9/2006 | Lionberger et al. | |
| 7,105,026 B2 | 9/2006 | Johnson et al. | |
| 7,115,131 B2 | 10/2006 | Engh et al. | |
| 7,121,832 B2 | 10/2006 | Hsieh et al. | |
| 7,141,053 B2 | 11/2006 | Rosa et al. | |
| D533,664 S | 12/2006 | Buttler et al. | |
| 7,169,185 B2 | 1/2007 | Sidebotham | |
| 7,174,282 B2 | 2/2007 | Hollister et al. | |

(56) References Cited

U.S. PATENT DOCUMENTS

| | | | |
|---|---|---|---|
| 7,176,466 B2 | 2/2007 | Rousso et al. | |
| 7,184,814 B2 | 2/2007 | Lang et al. | |
| 7,198,628 B2 | 4/2007 | Ondrla et al. | |
| 7,218,232 B2 | 5/2007 | DiSilvestro et al. | |
| 7,239,908 B1 * | 7/2007 | Alexander et al. | 600/427 |
| 7,241,315 B2 | 7/2007 | Evans | |
| 7,255,702 B2 | 8/2007 | Serra et al. | |
| 7,258,701 B2 | 8/2007 | Aram et al. | |
| 7,275,218 B2 | 9/2007 | Petrella et al. | |
| 7,282,054 B2 | 10/2007 | Steffensmeier et al. | |
| 7,294,133 B2 | 11/2007 | Zink et al. | |
| 7,297,164 B2 | 11/2007 | Johnson et al. | |
| 7,309,339 B2 | 12/2007 | Cusick et al. | |
| 7,333,013 B2 | 2/2008 | Berger | |
| 7,335,231 B2 | 2/2008 | McLean | |
| 7,371,260 B2 | 5/2008 | Malinin | |
| 7,383,164 B2 | 6/2008 | Aram et al. | |
| 7,385,498 B2 | 6/2008 | Dobosz | |
| 7,388,972 B2 | 6/2008 | Kitson | |
| 7,390,327 B2 | 6/2008 | Collazo et al. | |
| 7,392,076 B2 | 6/2008 | Moctezuma de La Barrera | |
| 7,427,200 B2 | 9/2008 | Noble et al. | |
| 7,427,272 B2 | 9/2008 | Richard et al. | |
| 7,468,075 B2 | 12/2008 | Lang et al. | |
| 7,474,223 B2 | 1/2009 | Nycz et al. | |
| 7,488,325 B2 | 2/2009 | Qian | |
| 7,494,510 B2 | 2/2009 | Zweymuller | |
| 7,517,365 B2 * | 4/2009 | Carignan et al. | 623/20.35 |
| 7,527,631 B2 | 5/2009 | Maroney et al. | |
| 7,534,263 B2 | 5/2009 | Burdulis, Jr. et al. | |
| 7,542,791 B2 | 6/2009 | Mire et al. | |
| 7,559,931 B2 | 7/2009 | Stone | |
| 7,575,602 B2 | 8/2009 | Amirouche et al. | |
| 7,578,851 B2 | 8/2009 | Dong et al. | |
| 7,582,091 B2 | 9/2009 | Duncan et al. | |
| 7,591,821 B2 | 9/2009 | Kelman | |
| 7,601,155 B2 | 10/2009 | Petersen | |
| 7,604,639 B2 | 10/2009 | Swanson | |
| 7,611,516 B2 | 11/2009 | Maroney | |
| 7,618,451 B2 * | 11/2009 | Berez et al. | 623/14.12 |
| 7,621,915 B2 | 11/2009 | Frederick et al. | |
| 7,625,409 B2 | 12/2009 | Saltzman et al. | |
| 7,646,161 B2 | 1/2010 | Albu-Schaffer et al. | |
| 7,651,501 B2 | 1/2010 | Penenberg et al. | |
| 7,670,345 B2 | 3/2010 | Plassky et al. | |
| 7,682,398 B2 | 3/2010 | Croxton et al. | |
| 7,695,477 B2 * | 4/2010 | Creger et al. | 606/87 |
| 7,695,521 B2 | 4/2010 | Ely et al. | |
| 7,699,847 B2 | 4/2010 | Sheldon et al. | |
| 7,704,253 B2 | 4/2010 | Bastian et al. | |
| 7,723,395 B2 | 5/2010 | Ringeisen et al. | |
| D622,854 S * | 8/2010 | Otto et al. | D24/155 |
| 7,780,672 B2 * | 8/2010 | Metzger et al. | 606/88 |
| 7,780,740 B2 | 8/2010 | Steinberg | |
| 7,794,466 B2 | 9/2010 | Merchant et al. | |
| 7,794,467 B2 | 9/2010 | McGinley et al. | |
| 7,794,504 B2 | 9/2010 | Case | |
| 7,806,896 B1 | 10/2010 | Bonutti | |
| 7,809,184 B2 | 10/2010 | Neubauer et al. | |
| 7,819,925 B2 | 10/2010 | King et al. | |
| 7,828,806 B2 | 11/2010 | Graf et al. | |
| 7,850,698 B2 | 12/2010 | Straszheim-Morley et al. | |
| 7,879,109 B2 | 2/2011 | Borden et al. | |
| 7,892,261 B2 | 2/2011 | Bonutti | |
| 7,896,921 B2 | 3/2011 | Smith et al. | |
| 7,926,363 B2 * | 4/2011 | Miller et al. | 73/862.041 |
| 7,935,119 B2 * | 5/2011 | Ammann et al. | 606/87 |
| 7,935,150 B2 * | 5/2011 | Carignan et al. | 623/20.35 |
| 7,938,861 B2 | 5/2011 | King et al. | |
| 7,959,637 B2 | 6/2011 | Fox et al. | |
| 7,962,196 B2 | 6/2011 | Tuma | |
| 7,963,968 B2 | 6/2011 | Dees, Jr. | |
| 7,967,823 B2 * | 6/2011 | Ammann et al. | 606/88 |
| 7,967,868 B2 * | 6/2011 | White et al. | 623/20.35 |
| 7,974,677 B2 | 7/2011 | Mire et al. | |
| 7,981,158 B2 | 7/2011 | Fitz et al. | |
| 7,993,353 B2 | 8/2011 | Rossner et al. | |
| 8,062,301 B2 | 11/2011 | Ammann et al. | |
| 8,066,708 B2 | 11/2011 | Lang et al. | |
| 8,070,752 B2 * | 12/2011 | Metzger et al. | 606/88 |
| 8,083,745 B2 | 12/2011 | Lang et al. | |
| 8,083,746 B2 | 12/2011 | Novak | |
| 8,083,749 B2 * | 12/2011 | Taber | 606/96 |
| 8,086,336 B2 | 12/2011 | Christensen | |
| 8,092,465 B2 * | 1/2012 | Metzger et al. | 606/96 |
| 8,133,230 B2 | 3/2012 | Stevens et al. | |
| 8,133,234 B2 * | 3/2012 | Meridew et al. | 606/91 |
| 8,137,406 B2 * | 3/2012 | Novak et al. | 623/20.32 |
| 8,160,345 B2 * | 4/2012 | Pavlovskaia et al. | 382/131 |
| 8,167,951 B2 | 5/2012 | Ammann et al. | |
| 8,170,641 B2 | 5/2012 | Belcher | |
| 8,182,489 B2 | 5/2012 | Horacek | |
| 8,192,441 B2 | 6/2012 | Collazo | |
| 8,192,495 B2 | 6/2012 | Simpson et al. | |
| 8,211,112 B2 | 7/2012 | Novak et al. | |
| 8,221,430 B2 | 7/2012 | Park et al. | |
| 8,241,292 B2 | 8/2012 | Collazo | |
| 8,241,293 B2 * | 8/2012 | Stone et al. | 606/87 |
| 8,265,790 B2 | 9/2012 | Amiot et al. | |
| D669,176 S | 10/2012 | Frey | |
| 8,282,646 B2 | 10/2012 | Schoenefeld et al. | |
| 8,298,237 B2 | 10/2012 | Schoenefeld et al. | |
| 8,303,596 B2 | 11/2012 | Plaβky et al. | |
| D672,038 S | 12/2012 | Frey | |
| 8,333,772 B2 | 12/2012 | Fox et al. | |
| 8,355,773 B2 | 1/2013 | Leitner et al. | |
| 8,377,066 B2 * | 2/2013 | Katrana et al. | 606/86 R |
| 8,398,646 B2 | 3/2013 | Metzger et al. | |
| 8,407,067 B2 | 3/2013 | Uthgenannt et al. | |
| 8,419,741 B2 * | 4/2013 | Carignan et al. | 606/88 |
| 8,430,931 B2 | 4/2013 | Acker et al. | |
| 8,439,675 B2 | 5/2013 | De Moyer | |
| 8,439,925 B2 | 5/2013 | Marino et al. | |
| 8,460,302 B2 | 6/2013 | Park et al. | |
| 8,473,305 B2 | 6/2013 | Belcher et al. | |
| 8,486,150 B2 | 7/2013 | White et al. | |
| 8,500,740 B2 | 8/2013 | Bojarski et al. | |
| 8,532,361 B2 * | 9/2013 | Pavlovskaia et al. | 382/131 |
| 8,532,807 B2 | 9/2013 | Metzger | |
| 8,535,387 B2 | 9/2013 | Meridew et al. | |
| 8,543,234 B2 | 9/2013 | Gao | |
| 8,568,487 B2 * | 10/2013 | Witt et al. | 623/22.12 |
| 8,591,516 B2 | 11/2013 | Metzger et al. | |
| 8,597,365 B2 | 12/2013 | Meridew | |
| 8,603,180 B2 * | 12/2013 | White et al. | 623/22.11 |
| 8,608,748 B2 * | 12/2013 | Metzger et al. | 606/88 |
| 8,608,749 B2 * | 12/2013 | Meridew et al. | 606/91 |
| 8,617,170 B2 | 12/2013 | Ashby et al. | |
| 8,617,175 B2 | 12/2013 | Park et al. | |
| 8,632,547 B2 * | 1/2014 | Maxson et al. | 606/88 |
| 8,668,700 B2 | 3/2014 | Catanzarite et al. | |
| 2001/0005797 A1 | 6/2001 | Barlow et al. | |
| 2001/0011190 A1 | 8/2001 | Park | |
| 2001/0021876 A1 | 9/2001 | Terrill-Grisoni et al. | |
| 2001/0054478 A1 | 12/2001 | Watanabe et al. | |
| 2002/0007294 A1 | 1/2002 | Bradbury et al. | |
| 2002/0029045 A1 | 3/2002 | Bonutti | |
| 2002/0052606 A1 | 5/2002 | Bonutti | |
| 2002/0059049 A1 * | 5/2002 | Bradbury et al. | 703/11 |
| 2002/0082741 A1 | 6/2002 | Mazumder et al. | |
| 2002/0087274 A1 * | 7/2002 | Alexander et al. | 702/19 |
| 2002/0092532 A1 | 7/2002 | Yoon | |
| 2002/0107522 A1 | 8/2002 | Picard et al. | |
| 2002/0128872 A1 | 9/2002 | Giammattei | |
| 2002/0147415 A1 | 10/2002 | Martelli | |
| 2002/0193797 A1 | 12/2002 | Johnson et al. | |
| 2002/0198528 A1 * | 12/2002 | Engh et al. | 606/79 |
| 2003/0009171 A1 | 1/2003 | Tornier | |
| 2003/0009234 A1 | 1/2003 | Treacy et al. | |
| 2003/0011624 A1 | 1/2003 | Ellis | |
| 2003/0018338 A1 | 1/2003 | Axelson et al. | |
| 2003/0039676 A1 | 2/2003 | Boyce et al. | |
| 2003/0055502 A1 * | 3/2003 | Lang et al. | 623/16.11 |
| 2003/0105526 A1 | 6/2003 | Bryant et al. | |

(56) References Cited

U.S. PATENT DOCUMENTS

| | | |
|---|---|---|
| 2003/0109784 A1* | 6/2003 | Loh et al. ................... 600/427 |
| 2003/0120276 A1 | 6/2003 | Tallarida et al. |
| 2003/0130741 A1* | 7/2003 | McMinn ................... 623/23.14 |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1* | 2/2004 | Noble et al. ................... 600/426 |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1* | 8/2004 | Sanford et al. ................... 606/88 |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0149283 A1 | 7/2006 | May et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0039205 A1* | 2/2007 | Erb et al. ................... 36/44 |
| 2007/0043582 A1* | 2/2007 | Peveto et al. ................... 705/1 |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |

(56) References Cited

U.S. PATENT DOCUMENTS

| | | |
|---|---|---|
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1* | 11/2007 | Mahfouz et al. .............. 606/102 |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1* | 1/2008 | Collazo ........................ 606/87 |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1* | 11/2008 | Kunz et al. ..................... 606/87 |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1* | 4/2009 | Aram et al. ..................... 606/79 |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1* | 4/2009 | Aram et al. ..................... 606/87 |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1* | 6/2009 | Meridew et al. ................ 606/88 |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1* | 9/2009 | Park et al. ..................... 606/89 |
| 2009/0222016 A1* | 9/2009 | Park et al. ..................... 606/89 |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1* | 10/2009 | White et al. ..................... 606/89 |
| 2009/0254367 A1 | 10/2009 | Belcher et al. |
| 2009/0259312 A1 | 10/2009 | Shterling et al. |
| 2009/0270868 A1* | 10/2009 | Park et al. ..................... 606/87 |

(56) References Cited

U.S. PATENT DOCUMENTS

| | | | |
|---|---|---|---|
| 2009/0274350 A1 | 11/2009 | Pavlovskaia et al. | |
| 2009/0287217 A1 | 11/2009 | Ammann et al. | |
| 2009/0287309 A1 | 11/2009 | Walch et al. | |
| 2009/0306676 A1 | 12/2009 | Lang et al. | |
| 2009/0307893 A1 | 12/2009 | Burdulis, Jr. et al. | |
| 2009/0318836 A1 | 12/2009 | Stone et al. | |
| 2009/0318921 A1 | 12/2009 | White et al. | |
| 2010/0010493 A1 | 1/2010 | Dower | |
| 2010/0016984 A1 | 1/2010 | Trabish | |
| 2010/0016986 A1 | 1/2010 | Trabish | |
| 2010/0023015 A1* | 1/2010 | Park | 606/87 |
| 2010/0030231 A1 | 2/2010 | Revie et al. | |
| 2010/0036404 A1 | 2/2010 | Yi et al. | |
| 2010/0042105 A1 | 2/2010 | Park et al. | |
| 2010/0049195 A1 | 2/2010 | Park et al. | |
| 2010/0057088 A1 | 3/2010 | Shah | |
| 2010/0076439 A1 | 3/2010 | Hatch | |
| 2010/0076505 A1 | 3/2010 | Borja | |
| 2010/0076563 A1 | 3/2010 | Otto et al. | |
| 2010/0076571 A1 | 3/2010 | Hatch | |
| 2010/0082034 A1 | 4/2010 | Remia | |
| 2010/0082035 A1 | 4/2010 | Keefer | |
| 2010/0082067 A1 | 4/2010 | Kondrashov | |
| 2010/0087829 A1 | 4/2010 | Metzger et al. | |
| 2010/0094295 A1 | 4/2010 | Schnieders et al. | |
| 2010/0105011 A1 | 4/2010 | Karkar et al. | |
| 2010/0121334 A1 | 5/2010 | Couture et al. | |
| 2010/0121335 A1 | 5/2010 | Penenberg et al. | |
| 2010/0137869 A1 | 6/2010 | Borja et al. | |
| 2010/0137924 A1 | 6/2010 | Tuke et al. | |
| 2010/0145343 A1 | 6/2010 | Johnson et al. | |
| 2010/0145344 A1 | 6/2010 | Jordan et al. | |
| 2010/0152782 A1 | 6/2010 | Stone et al. | |
| 2010/0160917 A1 | 6/2010 | Fitz et al. | |
| 2010/0168752 A1 | 7/2010 | Edwards | |
| 2010/0168754 A1 | 7/2010 | Fitz et al. | |
| 2010/0168857 A1 | 7/2010 | Hatch | |
| 2010/0179663 A1 | 7/2010 | Steinberg | |
| 2010/0185202 A1 | 7/2010 | Lester et al. | |
| 2010/0191244 A1 | 7/2010 | White et al. | |
| 2010/0198224 A1 | 8/2010 | Metzger et al. | |
| 2010/0212138 A1* | 8/2010 | Carroll et al. | 29/446 |
| 2010/0217109 A1 | 8/2010 | Belcher | |
| 2010/0217270 A1 | 8/2010 | Polinski et al. | |
| 2010/0217336 A1 | 8/2010 | Crawford et al. | |
| 2010/0217338 A1* | 8/2010 | Carroll et al. | 606/86 R |
| 2010/0228257 A1 | 9/2010 | Bonutti | |
| 2010/0249657 A1 | 9/2010 | Nycz et al. | |
| 2010/0249796 A1 | 9/2010 | Nycz | |
| 2010/0256649 A1 | 10/2010 | Capsal et al. | |
| 2010/0262150 A1 | 10/2010 | Lian | |
| 2010/0274253 A1 | 10/2010 | Ure | |
| 2010/0281678 A1 | 11/2010 | Burdulis, Jr. et al. | |
| 2010/0286700 A1 | 11/2010 | Snider et al. | |
| 2010/0292743 A1 | 11/2010 | Singhal et al. | |
| 2010/0298894 A1 | 11/2010 | Bojarski et al. | |
| 2010/0305574 A1 | 12/2010 | Fitz et al. | |
| 2010/0318088 A1 | 12/2010 | Warne et al. | |
| 2010/0324692 A1 | 12/2010 | Uthgenannt et al. | |
| 2011/0004317 A1 | 1/2011 | Hacking et al. | |
| 2011/0009869 A1 | 1/2011 | Marino et al. | |
| 2011/0015636 A1* | 1/2011 | Katrana et al. | 606/87 |
| 2011/0015639 A1* | 1/2011 | Metzger et al. | 606/91 |
| 2011/0015752 A1 | 1/2011 | Meridew | |
| 2011/0022049 A1 | 1/2011 | Huebner et al. | |
| 2011/0029091 A1 | 2/2011 | Bojarski et al. | |
| 2011/0029093 A1 | 2/2011 | Bojarski et al. | |
| 2011/0029116 A1 | 2/2011 | Jordan et al. | |
| 2011/0035012 A1* | 2/2011 | Linares | 623/18.11 |
| 2011/0040303 A1 | 2/2011 | Iannotti | |
| 2011/0040334 A1 | 2/2011 | Kaes et al. | |
| 2011/0046735 A1 | 2/2011 | Metzger et al. | |
| 2011/0054478 A1 | 3/2011 | Vanasse et al. | |
| 2011/0066193 A1* | 3/2011 | Lang et al. | 606/86 R |
| 2011/0066245 A1* | 3/2011 | Lang et al. | 623/18.11 |
| 2011/0071528 A1 | 3/2011 | Carson | |
| 2011/0071529 A1 | 3/2011 | Carson | |
| 2011/0071530 A1 | 3/2011 | Carson | |
| 2011/0071532 A1 | 3/2011 | Carson | |
| 2011/0071533 A1* | 3/2011 | Metzger et al. | 606/88 |
| 2011/0071581 A1 | 3/2011 | Lang et al. | |
| 2011/0087332 A1 | 4/2011 | Bojarski et al. | |
| 2011/0092804 A1 | 4/2011 | Schoenefeld et al. | |
| 2011/0093086 A1* | 4/2011 | Witt et al. | 623/22.15 |
| 2011/0106254 A1* | 5/2011 | Abel et al. | 623/16.11 |
| 2011/0125264 A1 | 5/2011 | Bagga et al. | |
| 2011/0130795 A1 | 6/2011 | Ball | |
| 2011/0151027 A1 | 6/2011 | Clineff et al. | |
| 2011/0151259 A1 | 6/2011 | Jarman-Smith et al. | |
| 2011/0153025 A1 | 6/2011 | McMinn | |
| 2011/0160736 A1 | 6/2011 | Meridew et al. | |
| 2011/0160867 A1* | 6/2011 | Meridew et al. | 623/20.36 |
| 2011/0166578 A1* | 7/2011 | Stone et al. | 606/88 |
| 2011/0172672 A1* | 7/2011 | Dubeau et al. | 606/87 |
| 2011/0184419 A1* | 7/2011 | Meridew et al. | 606/80 |
| 2011/0184526 A1 | 7/2011 | White et al. | |
| 2011/0190899 A1 | 8/2011 | Pierce et al. | |
| 2011/0190901 A1 | 8/2011 | Weissberg et al. | |
| 2011/0213376 A1 | 9/2011 | Maxson et al. | |
| 2011/0214279 A1 | 9/2011 | Park et al. | |
| 2011/0218545 A1 | 9/2011 | Catanzarite et al. | |
| 2011/0224674 A1* | 9/2011 | White et al. | 606/91 |
| 2011/0238071 A1 | 9/2011 | Fernandez-Scoma | |
| 2011/0251617 A1 | 10/2011 | Ammann et al. | |
| 2011/0257657 A1 | 10/2011 | Turner et al. | |
| 2011/0269100 A1 | 11/2011 | Furrer et al. | |
| 2011/0275032 A1* | 11/2011 | Tardieu et al. | 433/174 |
| 2011/0276145 A1* | 11/2011 | Carignan et al. | 623/20.35 |
| 2011/0282473 A1* | 11/2011 | Pavlovskaia et al. | 700/98 |
| 2011/0295887 A1 | 12/2011 | Palmese et al. | |
| 2011/0313424 A1* | 12/2011 | Bono et al. | 606/91 |
| 2011/0319745 A1 | 12/2011 | Frey | |
| 2012/0010619 A1 | 1/2012 | Barsoum | |
| 2012/0010710 A1 | 1/2012 | Frigg | |
| 2012/0010711 A1 | 1/2012 | Antonyshyn et al. | |
| 2012/0041445 A1 | 2/2012 | Roose et al. | |
| 2012/0041446 A1 | 2/2012 | Wong et al. | |
| 2012/0065640 A1 | 3/2012 | Metzger et al. | |
| 2012/0078254 A1 | 3/2012 | Ashby et al. | |
| 2012/0078258 A1 | 3/2012 | Lo et al. | |
| 2012/0078259 A1 | 3/2012 | Meridew | |
| 2012/0089595 A1 | 4/2012 | Jaecksch | |
| 2012/0101586 A1 | 4/2012 | Carson | |
| 2012/0109137 A1 | 5/2012 | Iannotti et al. | |
| 2012/0109138 A1* | 5/2012 | Meridew et al. | 606/91 |
| 2012/0109226 A1* | 5/2012 | Iannotti et al. | 606/86 R |
| 2012/0123422 A1 | 5/2012 | Agnihotri et al. | |
| 2012/0130382 A1* | 5/2012 | Iannotti et al. | 606/87 |
| 2012/0136365 A1 | 5/2012 | Iannotti et al. | |
| 2012/0141034 A1 | 6/2012 | Iannotti et al. | |
| 2012/0143197 A1* | 6/2012 | Lang et al. | 606/87 |
| 2012/0143267 A1 | 6/2012 | Iannotti et al. | 606/86 R |
| 2012/0158002 A1* | 6/2012 | Carignan et al. | 606/89 |
| 2012/0192401 A1* | 8/2012 | Pavlovskaia et al. | 29/428 |
| 2012/0209276 A1 | 8/2012 | Schuster | |
| 2012/0215225 A1 | 8/2012 | Philippon et al. | |
| 2012/0221017 A1 | 8/2012 | Bonutti | |
| 2012/0226283 A1* | 9/2012 | Meridew et al. | 606/81 |
| 2012/0232596 A1 | 9/2012 | Ribeiro | |
| 2012/0245587 A1 | 9/2012 | Fang et al. | |
| 2012/0259335 A1* | 10/2012 | Scifert et al. | 606/80 |
| 2012/0265208 A1* | 10/2012 | Smith | 606/87 |
| 2012/0271314 A1* | 10/2012 | Stemniski et al. | 606/87 |
| 2012/0271366 A1* | 10/2012 | Katrana et al. | 606/86 R |
| 2012/0276509 A1 | 11/2012 | Iannotti et al. | |
| 2012/0277751 A1 | 11/2012 | Catanzarite et al. | |
| 2012/0289965 A1 | 11/2012 | Gelaude et al. | |
| 2012/0296339 A1* | 11/2012 | Iannotti et al. | 606/87 |
| 2012/0303004 A1 | 11/2012 | Uthgenannt et al. | |
| 2012/0303033 A1 | 11/2012 | Weiner et al. | |
| 2012/0310399 A1* | 12/2012 | Metzger | 700/98 |
| 2012/0316564 A1* | 12/2012 | Serbousek et al. | 606/80 |
| 2012/0323246 A1* | 12/2012 | Catanzarite et al. | 606/88 |
| 2013/0001121 A1* | 1/2013 | Metzger | 206/438 |

(56) References Cited

U.S. PATENT DOCUMENTS

| | | | |
|---|---|---|---|
| 2013/0006250 A1* | 1/2013 | Metzger et al. | 606/87 |
| 2013/0035766 A1 | 2/2013 | Meridew | |
| 2013/0046310 A1* | 2/2013 | Ranawat et al. | 606/91 |
| 2013/0060253 A1 | 3/2013 | Couture et al. | |
| 2013/0085500 A1* | 4/2013 | Meridew et al. | 606/89 |
| 2013/0119579 A1* | 5/2013 | Iannotti et al. | 264/259 |
| 2013/0123850 A1 | 5/2013 | Schoenefeld et al. | |
| 2013/0131681 A1* | 5/2013 | Katrana et al. | 606/87 |
| 2013/0144392 A1* | 6/2013 | Hughes | 623/18.11 |
| 2013/0197528 A1 | 8/2013 | Zakaria et al. | |
| 2013/0197687 A1* | 8/2013 | Pavlovskaia et al. | 700/118 |
| 2013/0218163 A1 | 8/2013 | Frey | |
| 2013/0289730 A1 | 10/2013 | Gabriel et al. | |
| 2013/0317511 A1 | 11/2013 | Bojarski et al. | |
| 2013/0338673 A1 | 12/2013 | Keppler | |
| 2014/0005672 A1 | 1/2014 | Edwards et al. | |
| 2014/0052270 A1 | 2/2014 | Witt et al. | |
| 2014/0081275 A1 | 3/2014 | Metzger et al. | |
| 2014/0088724 A1 | 3/2014 | Meridew | |
| 2014/0094816 A1 | 4/2014 | White et al. | |
| 2014/0100578 A1 | 4/2014 | Metzger et al. | |
| 2014/0107651 A1 | 4/2014 | Meridew et al. | |
| 2014/0107654 A1 | 4/2014 | Kehres et al. | |
| 2014/0107715 A1 | 4/2014 | Heilman et al. | |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6-233790 A | 8/1994 |
| JP | 2000245758 A | 9/2000 |
| JP | 2009514612 A | 4/2009 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A2 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |

(56) References Cited

FOREIGN PATENT DOCUMENTS

| WO | WO-2010144705 A1 | 12/2010 |
|---|---|---|
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

International Search Report and Written Opinion mailed Oct. 14, 2013 for PCT/US2013/057097 claiming benefit of U.S. Appl. No. 13/597,478, filed Aug. 29, 2012.
Biomet "Oxford® Partial Knee" brochure, 8 pages (Feb. 2011).
Biomet "The Oxford® Partial Knee Surgical Technique," brochure, pp. 1-38, (Feb. 2010).
Biomet, "Oxford® Partial Knee Microplasty® Instrumentation Surgical Technique", brochure, pp. 1-54 (May 2011).
International Preliminary Report on Patentability and Written Opinion mailed Sep. 7, 2012 for PCT/US2011/026333 claiming benefit of U.S. Appl. No. 12/714,023, filed Feb. 26, 2010.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (Oct. 31, 1999) 16 sheets.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (Dec. 31, 2008) pp. 1-25.
"Discovery® Elbow System," brochure. Biomet Orthopedics, Inc. (Nov. 30, 2007) 3 sheets.
"Hipsextant Instructions of Use." (2011) Surgical Planning Associates, Inc. 19 pages.
"Knee tensor combined with laser femoral head locator," Research Disclosure. Jul. 2006. Number 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (Mar. 31, 2004) pp. 1-8 (12 sheets).
"Patient Matched PMI Implants, C.A.M.R.A. 3-D Imaging," brochure, Biomet, Inc. (Jan. 31, 1991) 6 pages.
"Regenerex® Tibial Cone Augment, Surgical Technique Addendum to the Vanguard® SSK Revision System," brochure. Biomet® Orthopedics. (Mar. 31, 2010) pp. 1-8 (12 sheets).
"Signature™ Personalized Patient Care, Surgical Technique Addendum to the Vanguard Knee System" brochure. Biomet® Orthopedics, Inc. (May 15, 2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (Aug. 31, 2010) pp. 1-25.
"Zimmer® UniSpacer® Knee System," brochure. (2005) Zimmer, Inc. 4 sheets.
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Great Britain Search Report mailed Dec. 21, 2011 for GB1116054.6, claiming benefit of U.S. Appl. No. 12/888,005, filed Sep. 22, 2010.
Haaker, R.G., et al., "Minimal-invasive navigiert implantierte unikondyläre Knieendoprothese," Orthopäde 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, a New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report and Written Opinion mailed Jan. 5, 2012 for PCT/US2010/038845 claiming benefit of U.S. Appl. No. 12/486,992, filed Jul. 18, 2009.
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Dec. 22, 2011 for PCT/US2010/038177 claiming benefit of U.S. Appl. No. 12/483,807, filed Jun. 12, 2009.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.
International Preliminary Report on Patentability for PCT/US2010/050701 mailed Apr. 12, 2012 claiming benefit of U.S. Appl. No. 12/571,969, filed Oct. 1, 2009.
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Mar. 31, 2011 for PCT/US2009/056670 claiming benefit of U.S. Appl. No. 12/211,407, filed Sep. 16, 2008.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.

(56) References Cited

OTHER PUBLICATIONS

International Search Report and Written Opinion for PCT/US2009/056670 mailed Mar. 2, 2010 claiming benefit of U.S. Appl. No. 12/211,407, filed Sep. 16, 2008.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Aug. 9, 2011 for PCT/US2011/026333 claiming benefit of U.S. Appl. No. 12/714,023, filed Feb. 26, 2010.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 10, 2010 for PCT/US2010/038177 claiming benefit of U.S. Appl. No. 12/483,807, filed Jun. 12, 2009.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed Mar. 5, 2012 for PCT/US2011/057300 claiming benefit of U.S. Appl. No. 12/938,905, filed Nov. 3, 2010.
International Search Report and Written Opinion mailed May 8, 2012 for PCT/US2012/026356 claiming benefit of U.S. Appl. No. 13/041,883, filed Mar. 7, 2011.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Oct. 5, 2010 for PCT/US2010/038845 claiming benefit of U.S. Appl. No. 12/486,992, filed Jun. 18, 2009.
International Search Report mailed Nov. 30, 2010 for PCT/EP2010/061630 filed Aug. 10, 2010 claiming benefit of DE102009028503.2 filed Aug. 13, 2009.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-158. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsaulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.
Schuller-Götzburg, P., et al., 3D-Implantatplanung und Stereolithographie-Implantatbohrschablonen, Stomatologie 101.3, pp. 55-59 (May 2004).
Sharp, S. Michael, Ph.D., Patient-Specific, Resurfacing Bi-Compartmental Arthuroplasty, Futuretech, Orthopaedic Product News (Mar./Apr. 2008) pp. 12-15.
Sisto, Domenick, J., et al., "Custom Patellofemoral Arthroplasty of the Knee Surgical Technique," Journal of Bone and Joint Surgery, vol. 89-A, pp. 214-225 (Jul. 2006).
Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE... accessed Jul. 31, 2008.
Steinwachs, Matthias Reinhard, "Cartilage Repair—Autologous Chondrocyte Transplantation and Autologous Matrix-induced Chondrogenesis," European Musculoskeletal Review (2006) pp. 65-68.
Supplementary European Search Report mailed Nov. 15, 2011 for EP07809326, which claims benefit of PCT/US2007/013223, filed Jun. 5, 2007; which claims benefit of U.S. Appl. No. 11/756,057, filed May 31, 2007.
Thoma, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensive® Shoulder System Surgical Technique," Biomet Orthopedics brochure (2007), pp. 1-53.

(56) References Cited

OTHER PUBLICATIONS

"Comprehensive® Total Shoulder System," Biomet Orthopedics brochure (2011), 4 pages.

Friedman, R.J. et al., "The Use of Computerized Tomography in the Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478, filed Aug. 29, 2011.

International Search Report and Written Opinion mailed Feb. 6, 2013 for PCT/US2012/060842, which claims benefit of U.S. Appl. No. 13/653,868, filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability and Written Opinion mailed Jan. 3, 2014 for PCT/US2012/042081 claiming benefit of U.S. Appl. No. 13/493,509, filed Jun. 11, 2012.

International Preliminary Report on Patentability and Written Opinion mailed Nov. 28, 2013 for PCT/US2012/038351 claiming benefit of U.S. Appl. No. 13/111,007, filed May 19, 2011.

International Preliminary Report on Patentability and Written Opinion mailed Apr. 24, 2014 for PCT/US2012/059189 claiming benefit of U.S. Appl. No. 13/597,478, filed Aug. 29, 2012.

International Preliminary Report on Patentability and Written Opinion mailed Mar. 13, 2014 for PCT/US2012/052853 claiming benefit of U.S. Appl. No. 13/221,968, filed Aug. 31, 2011.

International Search Report and Written Opinion mailed Apr. 14, 2014 for PCT/US2013/067505 claiming benefit of U.S. Appl. No. 13/718,129, filed Dec. 18, 2012.

Invitation to Pay Additional Fees mailed Feb. 6, 2014 for PCT/US2013/067505, which claims benefit of U.S. Appl. No. 13/718,129, filed Dec. 18, 2012.

Signature™ Personalized Patient Care, Surgical Technique Addendum Vanguard® Complete Knee System, Biomet® Orthopedics Brochure, (2011), p. 1-32.

\* cited by examiner

PATIENT-SPECIFIC ACETABULAR GUIDE AND METHOD

CROSS-REFERENCE TO RELATED APPLICATIONS

This application is a divisional of U.S. patent application Ser. No. 12/389,901, filed Feb. 20, 2009, which is: (A) a continuation-in-part of U.S. patent application Ser. No. 11/756,057, filed on May 31, 2007, which claims the benefit of U.S. Provisional Application No. 60/812,694, filed on Jun. 9, 2006; and (B) a continuation-in-part of U.S. patent application Ser. No. 12/211,407, filed Sep. 16, 2008, which is a continuation-in-part of U.S. patent application Ser. No. 11/971,390, filed on Jan. 9, 2008, now U.S. Pat. No. 8,070,752, issued on Dec. 6, 2011, which is a continuation-in-part of U.S. patent application Ser. No. 11/363,548, filed on Feb. 27, 2006, now U.S. Pat. No. 7,780,672, issued on Aug. 24, 2010.

The disclosures of the above applications are incorporated herein by reference.

INTRODUCTION

Various custom made, patient-specific orthopedic implants and associated templates and guides are known in the art. Such implants and guides can be developed using commercially available software. Custom implant guides are used to accurately place pins, guide bone cuts, and insert implants during orthopedic procedures. The guides are made from a pre-operative plan formed from an MRI or CT scan of the patient and rely on matching a subcutaneous anatomic feature for correct positioning.

The present teachings provide a patient-specific guide for guiding an acetabular implant into the acetabulum.

SUMMARY

The present teachings provide an acetabular system. In one aspect, the acetabular system includes an acetabular guide having a first surface and a second surface opposite to the first surface, the first surface made to conform to an acetabular rim surface around an acetabulum of a patient in accordance with a three-dimensional image of the acetabulum of the patient. The acetabular guide includes an aperture having an inner surface oriented at selected anteversion and abduction angles relative to the first surface for guiding an acetabular implant into the acetabulum at the selected anteversion and abduction angles.

The present teachings also provide an acetabular system. The acetabular system includes an annular acetabular guide and an acetabular inserter. The acetabular guide includes a first surface and a second surface opposite to the first surface, the first surface being patient-specific and made to conform to an acetabular rim surface around an acetabulum of a patient in accordance with a three-dimensional image of the acetabulum of the patient. The acetabular guide has a cylindrical inner surface oriented at selected anteversion and abduction angles relative to the first surface. The acetabular inserter includes a guide-engaging portion with a cylindrical outer surface mateable with the cylindrical inner surface of the acetabular guide.

The present teachings also provide a method for inserting an acetabular cup into an acetabulum of a patient. The method includes inspecting a preoperative plan including a three-dimensional image of a patient's acetabulum, selecting at least one of a patient-specific anteversion angle and a patient-specific abduction angle, and approving the preoperative plan. The method also includes preparing the patient's acetabulum for implantation, positioning a patient-specific first surface of an acetabular guide around a matched acetabular rim surface of the patient, and inserting an acetabular cup through an opening of the acetabular guide, the opening having a cylindrical inner surface oriented at the selected at least one of the patient-specific anteversion angle and patient-specific abduction angle.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

Figure 1:
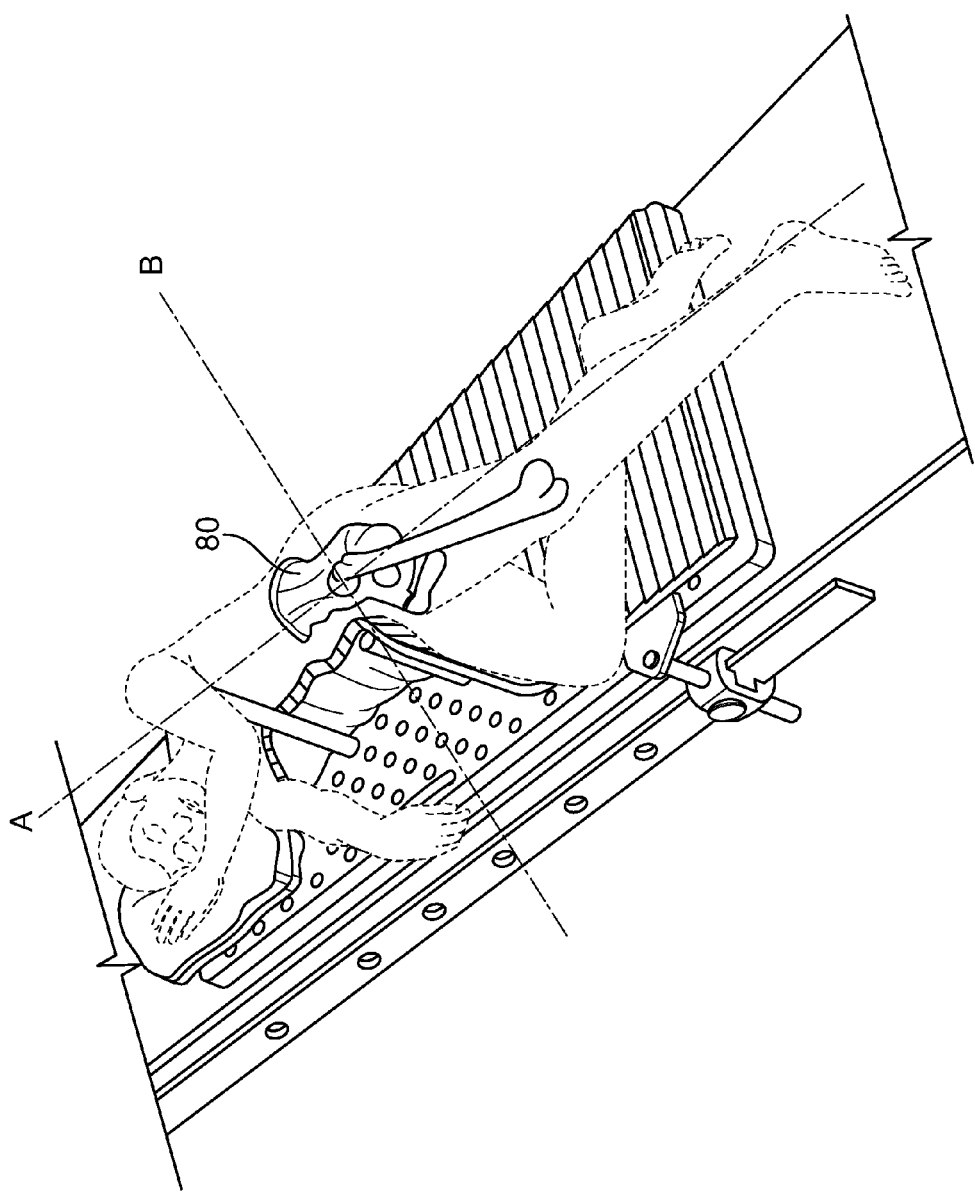
FIG. 1 is an exemplary illustration of a patient in preparation of an acetabular implant procedure.

The following description is merely exemplary in nature and is in no way intended to limit the present teachings, applications, or uses.

The present teachings generally provide a patient-specific acetabular guide and associated inserter for use in orthopedic surgery, such as in joint replacement or revision surgery, for example. The patient-specific alignment guides can be used either with conventional or patient-specific implant components prepared with computer-assisted image methods. Computer modeling for obtaining three dimensional images of the patient's anatomy using MRI or CT scans of the patient's anatomy, the patient-specific prosthesis components, and the patient-specific guides and templates can be provided by various CAD programs and/or software available, for example, by Materialise USA, Ann Arbor, Mich.

Patient-specific alignment guides and implants are generally configured to match the anatomy of a specific patient. The patient-specific alignment guides are generally formed using computer modeling based on the patient's 3-D anatomic image and have an engagement surface that is made to conformingly contact and match a three-dimensional image of the patient's bone surface (with or without cartilage or other soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan. The patient-specific alignment guides can be used in minimally invasive surgery, and in particular in surgery with multiple minimally-invasive incisions. Various alignment guides and preoperative planning procedures are disclosed in commonly assigned and co-pending U.S. patent application Ser. No. 11/756,057, filed on May 31, 2007; U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; and U.S. patent application Ser. No. 12/025,414, filed Feb. 4, 2008. The disclosures of the above applications are incorporated herein by reference.

As disclosed, for example, in above-referenced U.S. patent application Ser. No. 11/756,057, filed on May 31, 2007; in the preoperative planning stage for a joint replacement or revision procedure, an MRI scan or a series of CT scans of the relevant anatomy of the patient, such as, for example, the entire leg of the joint to be reconstructed, can be performed at a medical facility or doctor's office. The scan data obtained can be sent to a manufacturer. The scan data can be used to construct a three-dimensional image of the joint and provide an initial implant fitting and alignment in a computer file form or other computer representation. The initial implant fitting and alignment can be obtained using an alignment method, such as alignment protocols used by individual surgeons.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review. The surgeon can incrementally manipulate the position of images of implant components in an interactive image of the joint. Additionally, the surgeon can select or modify resection planes, types of implants and orientations of implant insertion. For example, the surgeon may select patient-specific anteversion and abduction angles for acetabular implants, as discussed below. After the surgeon modifies and/or approves the surgical plan, the surgeon can send the final, approved plan to the manufacturer.

After the surgical plan is approved by the surgeon, patient-specific alignment guides can be developed using a CAD program or other imaging software, such as the software provided by Materialise, for example, according to the surgical plan. Computer instructions of tool paths for machining the patient-specific alignment guides can be generated and stored in a tool path data file. The tool path can be provided as input to a CNC mill or other automated machining system, and the alignment guides can be machined from polymer, ceramic, metal or other suitable material, and sterilized. The sterilized alignment guides can be shipped to the surgeon or medical facility, for use during the surgical procedure.

The present teachings provide a patient-specific acetabular guide and associated inserter for inserting an acetabular implant in the acetabulum of a patient's pelvis in a guided orientation at least about first and second non-parallel anatomic axes. Referring to FIGS. 1, 3A and 3B, the first anatomic axis indicated at "A", passes through the acetabulum 82 of a patient's pelvis 80 (only half of the pelvis is shown) and is oriented generally in a superior/inferior direction relative to the patient. The second anatomic axis is indicated at "B" and is substantially perpendicular to the first axis A. As described below, the present teachings provide instruments and methods for guiding, orienting and positioning an acetabular implant 200 at a selected angle of anteversion relative to the axis A, as shown in FIG. 3A, and at a selected angle of abduction relative to the axis B, as also shown in FIG. 3B. The anteversion and abduction angles can be determined interactive or other surgeon input and can be patient-specific.

Figure 1A:
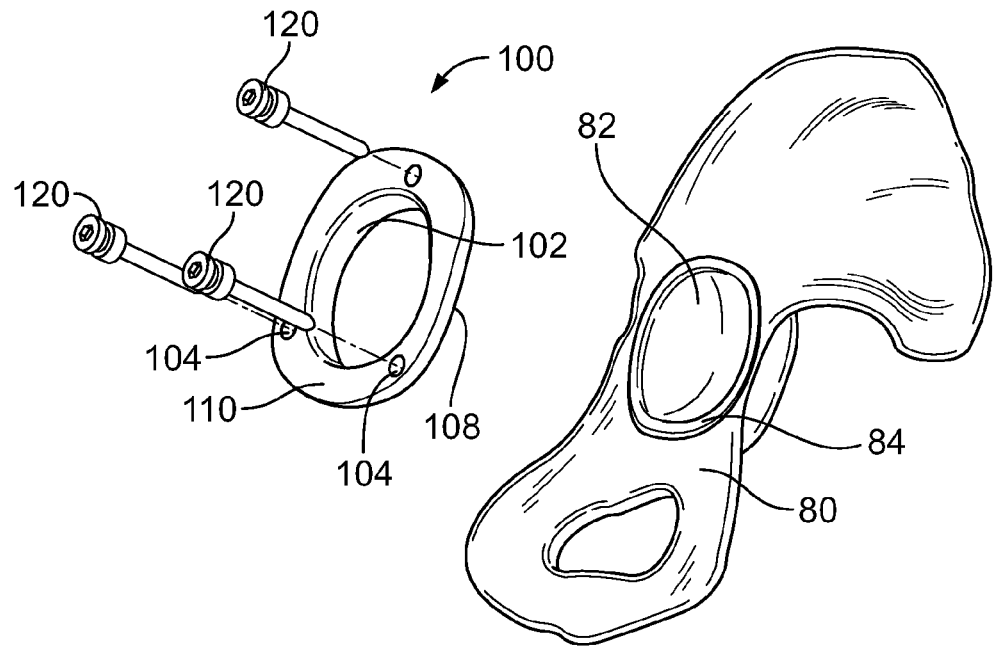
FIG. 1A is a perspective view of an acetabular guide according to the present teachings, the acetabular guide shown in relation to a patient's anatomy.

Referring to FIG. 1A, an exemplary acetabular guide 100 according to the present teachings can include a first surface 108 for engaging an area surrounding the acetabulum 82 and a second surface 110 opposite to the first surface 108. The acetabulum-engaging first surface 108 can be custom-made or patient-specific to conform and mirror an acetabular rim surface 84 around the acetabulum 82 of a specific patient by using three-dimensional image of the acetabulum and surrounding pelvic area of the patient, as described above. The first surface 108 enables the acetabular guide to nest or closely mate relative to the acetabulum 82 of the patient.

Figure 2:
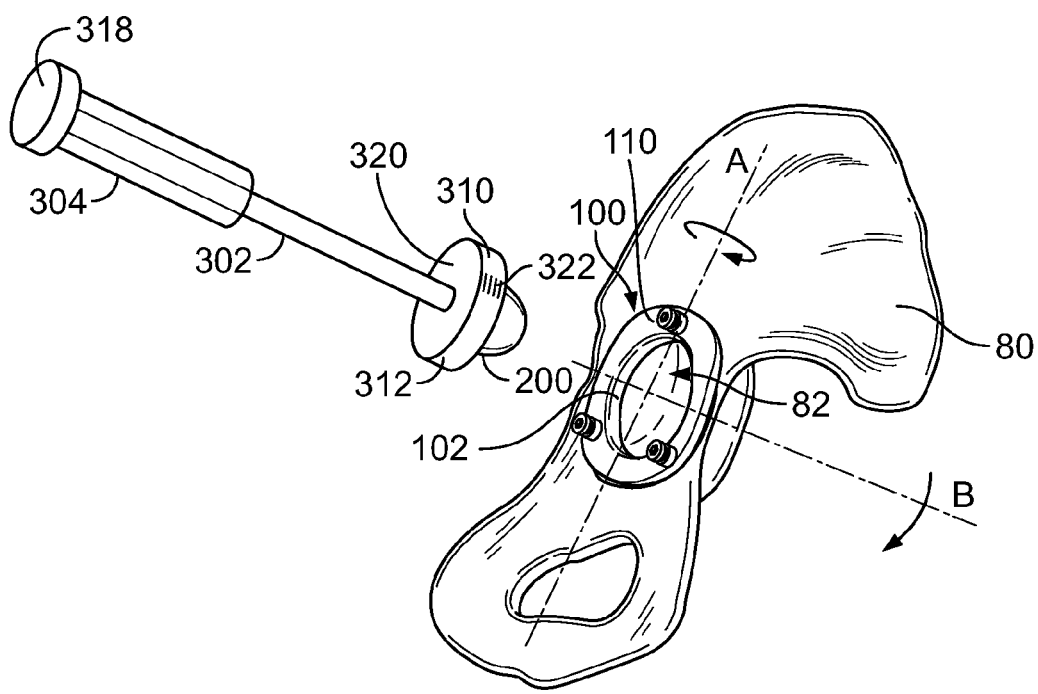
FIG. 2 is an environmental perspective view of the acetabular guide of FIG. 1A shown with an acetabular inserter holding an acetabular implant according to the present teachings.

The acetabular guide 100 can be temporarily and removably attached to the pelvis 80 using temporary fasteners 120, such as bone nails or tacks, for example, passing through corresponding holes 104 through the acetabular guide 100. The acetabular guide 100 can be annular with an opening defined by an inner surface 102. The inner surface 102 can be, for example, a cylindrical surface. The inner surface 102 can be oriented relative to the first and second surfaces 108, 110 of the acetabular guide 100 to provide a selected anteversion angle about the first axis A and a selected abduction angle relative to the axis B, as shown in FIGS. 2, 3A and 3B. The anteversion and abduction angles can be surgeon-selected and patient-specific and can be determined with surgeon input during the preoperative planning for the specific patient. Anteversion angles can be, for example, in the range of about 10-20 degrees forward relative to the first axis A, and adduction angles can be in the range of about 40-50 degrees downward relative to the second axis B.

Figure 3:
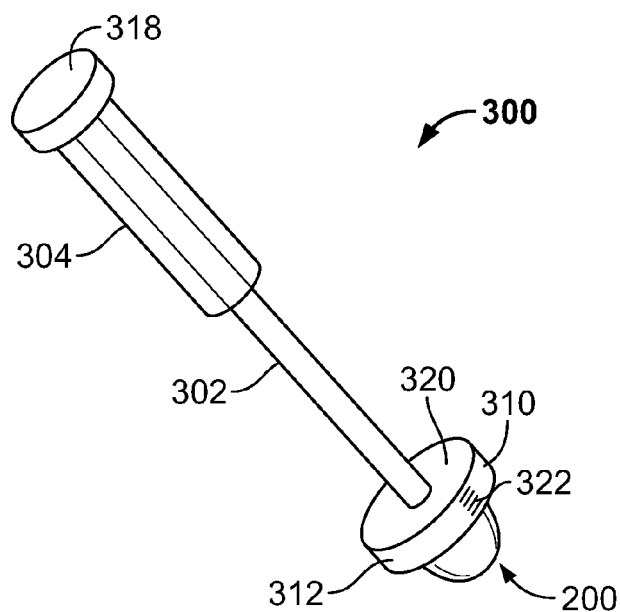
FIG. 3 is a perspective view of the acetabular inserter and acetabular implant of FIG. 2.
Figure 3A:
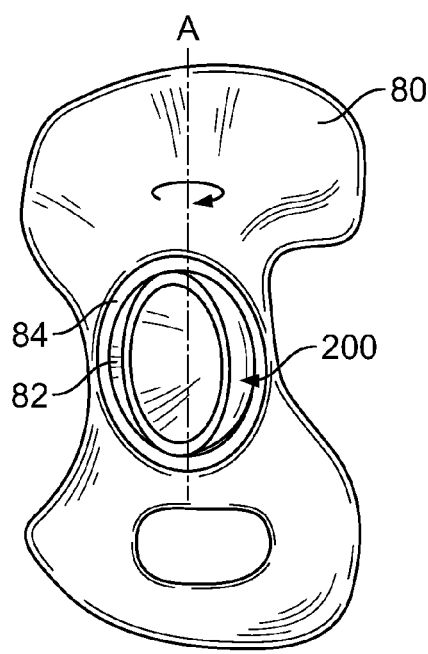
FIG. 3A is a perspective environmental view of an acetabular implant illustrating rotation about an anatomic axis A during insertion according to the present teachings.
Figure 3B:
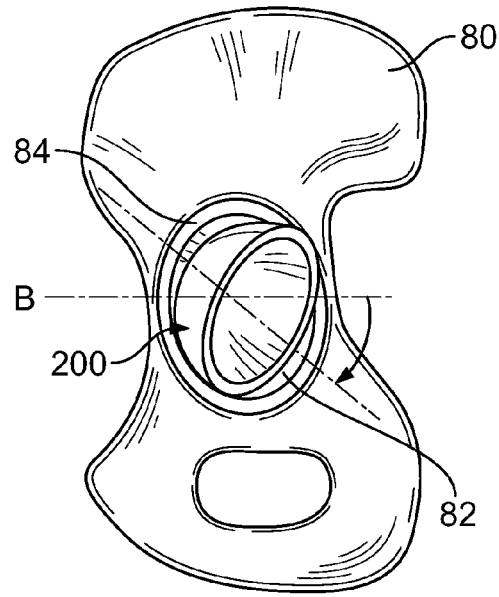
FIG. 3B is a perspective environmental view of an acetabular implant illustrating rotation about an anatomic axis B during insertion according to the present teachings.
Figure 4:
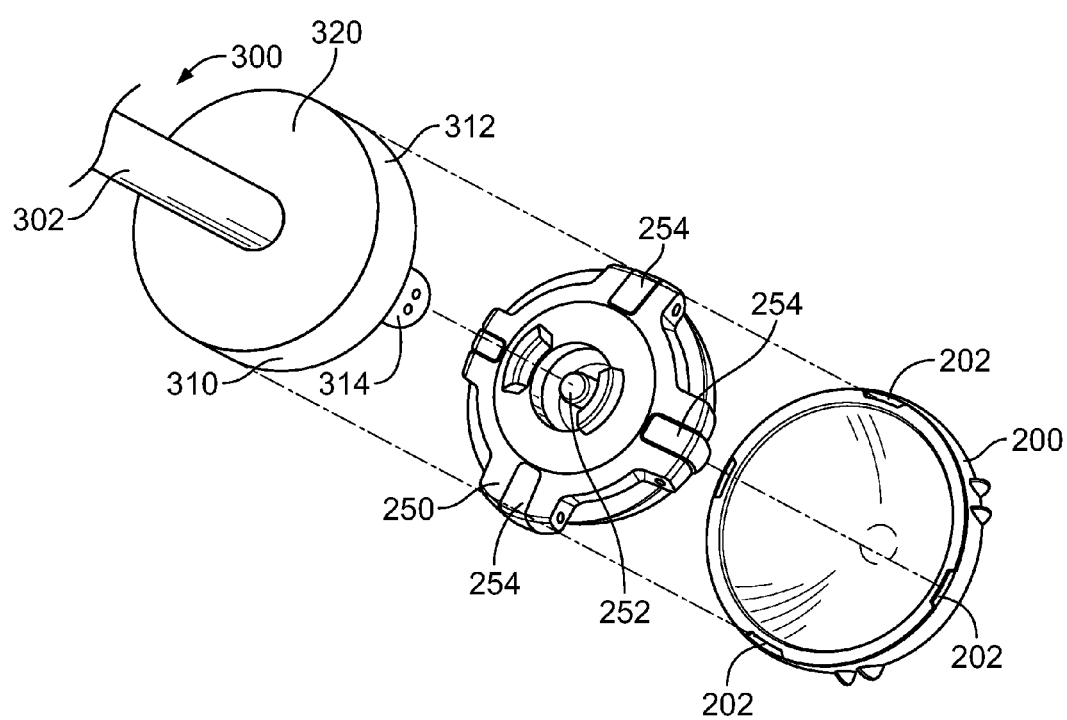
FIG. 4 is an exploded view of the acetabular inserter and acetabular implant of FIG. 3.

Referring to FIGS. 2-4, the acetabular guide 100 can be attached to the pelvis 80 around the acetabulum 72 after the acetabulum 82 has been reamed and prepared for receiving the acetabular implant 200, such as the Magnum™ acetabular cup commercially available from Biomet, Inc., Warsaw, Ind. The acetabular implant 200 can be inserted into the prepared acetabulum 82 using an inserter 300 according to the present teachings. The inserter 300, which can also function as an impactor, can include a handle 304 with a proximal impaction surface 318, a shaft 302 and a guide-engaging portion 310 having a surface with a flat or planar portion 320. The guide-engaging portion 310 can have an outer surface 312, which conforms to and is mateable with the inner surface 102 of the acetabular guide 100 for guiding the acetabular implant 200. The inner surface 102 and the outer surface 312 can be cylindrical.

Referring to FIG. 4, the inserter 300 can engage the acetabular implant 200 via an intermediate member 250, such as the intermediate member of the Magnum™ system, which is commercially available from Biomet, Inc., Warsaw, Ind. More specifically, the inserter 300 can include a distal portion 314, such as a ball-bearing bushing, which can be inserted and engage a receptacle 252 of the intermediate member 250. The acetabular implant 200 can be mounted on the inserter 300 by aligning a plurality of fingers 254 of the intermediate member 250 with corresponding cut-outs 202 on a peripheral edge of the acetabular implant 200. The acetabular implant 200 can be secured to the inserter 300 by rotating the acetabular implant 200 relative to the insert 300 until a hand-tight fit is obtained.

Referring to FIG. 2, the inserter 300 with the acetabular implant 200 mounted thereon can be directed toward the acetabular guide 100. The outer surface 312 of the guide engaging portion 310 of the inserter 300 can be brought into contact with the inner surface 102 of the acetabular guide 100, guiding the acetabular implant 200 toward the selected anteversion and abduction orientation through the acetabular guide 100. The outer surface 312 of the guide engaging portion 310 can also provide an impaction-depth feedback by alignment with the inner surface 102 of the acetabular guide. Full impaction of the acetabular implant 200 into the acetabulum 82 can be indicated when planar portion 320 and/or outer surface 312 of the guide-engaging portion 310 of the inserter 300 are flush with and do not protrude over and above the second surface 110 of the acetabular guide 100. Depth indicia 322 can also be provided on the inserter shaft 302 or on the guide-engaging portion 310 of the inserter 300, as shown in FIG. 2.

After the acetabular implant 200 is fully seated in the acetabulum 82 in the selected anteversion and abduction orientations, the inserter 300 and intermediate member 250 can be removed. The temporary fasteners 120 can be removed and the acetabular guide released.

The acetabular guide 100 can be made of any biocompatible material, such as metal, ceramic or polymer. The acetabular guide 100 can be constructed by various manufacturing methods depending of the selected material, including, for example, machining, casting, molding, stereolithography or other layer deposition methods. In one aspect, the acetabular guide 100 can be made of disposable plastic material.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for inserting an acetabular cup into an acetabulum of a patient, the method comprising:
    positioning a first surface of an acetabular guide around an acetabular rim surface of an acetabulum of the patient, the first surface preoperatively configured as a mirror surface of the acetabular rim surface of the patient from a three-dimensional image of the acetabulum of the patient, the acetabular guide including an aperture having an inner surface oriented at preoperatively determined and patient-specific anteversion and abduction angles relative to the first surface;
    coupling an acetabular cup to a distal portion of an acetabular inserter;
    contacting an outer surface of a guide-engaging portion of the acetabular inserter to the inner surface of the acetabular guide, the outer surface preoperatively configured to mate with the inner surface at the patient-specific anteversion and abduction angles; and
    seating the acetabular cup to the acetabulum at the selected anteversion and abduction angles.

2. A method for inserting an acetabular cup into an acetabulum of a patient, the method comprising:
    positioning a first surface of an acetabular guide around an acetabular rim surface of an acetabulum of the patient, the first surface preoperatively configured as a mirror surface of the acetabular rim surface of the patient from a three-dimensional image of the acetabulum of the patient, the acetabular guide including an aperture having an inner surface oriented at preoperatively determined and patient-specific anteversion and abduction angles relative to the first surface;
    coupling an acetabular cup to a distal portion of an acetabular inserter;
    contacting an outer surface of a guide-engaging portion of the acetabular inserter to the inner surface of the acetabular guide, the outer surface preoperatively configured to mate with the inner surface at the patient-specific anteversion and abduction angles; and
    seating the acetabular cup to the acetabulum at the selected anteversion and abduction angles,
    wherein coupling the acetabular cup to the distal portion of the acetabular inserter includes rotating the acetabular cup relative to the inserter.

3. The method of claim 2, further comprising:
    impacting the acetabular inserter.

4. The method of claim 3, further comprising:
    determining a depth of impaction of the acetabular cup.

5. The method of claim 4, wherein determining the depth of impaction of the acetabular cup includes aligning a planar portion of the guide-engaging portion of the acetabular inserter relative to the first surface of the acetabular guide.

6. The method of claim 4, wherein determining the depth of impaction of the acetabular cup includes impacting the acetabular inserter to a depth determined by depth indicia marked on the acetabular inserter.

7. The method of claim 6, wherein the depth indicia are provided on the guide-engaging portion of the acetabular inserter.

8. The method of claim 3, wherein impacting the acetabular inserter includes impacting a proximal impaction surface of a handle of the acetabular inserter.

9. The method of claim 2, wherein the inner surface of the acetabular guide and the outer surface of the guide-engaging portion of the acetabular inserter are cylindrical.

10. A method for inserting an acetabular cup into an acetabulum of a patient, the method comprising:
    positioning a first surface of an acetabular guide around an acetabular rim surface of an acetabulum of the patient, the first surface preoperatively configured as a mirror surface of the acetabular rim surface of the patient from a three-dimensional image of the acetabulum of the patient, the acetabular guide including an aperture having an inner surface oriented at preoperatively determined and patient-specific anteversion and abduction angles relative to the first surface;
    coupling an acetabular cup to a distal portion of an acetabular inserter;
    contacting an outer surface of a guide-engaging portion of the acetabular inserter to the inner surface of the acetabular guide, the outer surface preoperatively configured to mate with the inner surface at the patient-specific anteversion and abduction angles; and
    seating the acetabular cup to the acetabulum at the selected anteversion and abduction angles, wherein coupling the acetabular cup to the distal portion of the acetabular inserter includes aligning a plurality of fingers of an intermediate member with corresponding cut-outs on a peripheral edge of the acetabular cup.

11. The method of claim 10, further comprising engaging a receptacle of the intermediate member with a bushing of the acetabular inserter.

12. A method for inserting an acetabular cup into an acetabulum of a patient, the method comprising:
   coupling a distal portion of an acetabular inserter to an intermediate member;
   connecting an acetabular cup to the intermediate member;
   positioning a first surface of an acetabular guide around an acetabular rim surface of an acetabulum of the patient, the first surface preoperatively configured as a mirror surface of the acetabular rim surface of the patient from a three-dimensional image of the acetabulum of the patient, the acetabular guide including an aperture having an inner surface oriented at preoperatively determined and patient-specific anteversion and abduction angles relative to the first surface;
   mateably contacting an outer surface of a guide-engaging portion of the acetabular inserter to the inner surface of the acetabular guide at the patient-specific anteversion and abduction angles; and
   inserting the acetabular cup into the acetabulum at the selected anteversion and abduction angles.

13. A method for inserting an acetabular cup into an acetabulum of a patient, the method comprising:
   coupling a distal portion of an acetabular inserter to an intermediate member;
   connecting an acetabular cup to the intermediate member;
   positioning a first surface of an acetabular guide around an acetabular rim surface of an acetabulum of the patient, the first surface preoperatively configured as a mirror surface of the acetabular rim surface of the patient from a three-dimensional image of the acetabulum of the patient, the acetabular guide including an aperture having an inner surface oriented at preoperatively determined and patient-specific anteversion and abduction angles relative to the first surface;
   mateably contacting an outer surface of a guide-engaging portion of the acetabular inserter to the inner surface of the acetabular guide at the patient-specific anteversion and abduction angles;
   inserting the acetabular cup into the acetabulum at the selected anteversion and abduction angles; and
   coupling a bushing of the acetabular inserter to a receptacle of the intermediate member.

14. The method of claim 13, further comprising:
   impacting a proximal impaction surface of the acetabular inserter to a predetermined depth by aligning a planar portion of the guide-engaging portion of the acetabular inserter relative to the first surface of the acetabular guide.

15. A method for inserting an acetabular cup into an acetabulum of a patient, the method comprising:
   coupling a distal portion of an acetabular inserter to an intermediate member;
   connecting an acetabular cup to the intermediate member;
   positioning a first surface of an acetabular guide around an acetabular rim surface of an acetabulum of the patient, the first surface preoperatively configured as a mirror surface of the acetabular rim surface of the patient from a three-dimensional image of the acetabulum of the patient, the acetabular guide including an aperture having an inner surface oriented at preoperatively determined and patient-specific anteversion and abduction angles relative to the first surface;
   mateably contacting an outer surface of a guide-engaging portion of the acetabular inserter to the inner surface of the acetabular guide at the patient-specific anteversion and abduction angles;
   inserting the acetabular cup into the acetabulum at the selected anteversion and abduction angles; and
   aligning a plurality of fingers of the intermediate member with corresponding cut-outs on a peripheral edge of the acetabular cup.

16. The method of claim 15, further comprising impacting a proximal impaction surface of the acetabular inserter to a depth determined by depth indicia on the guide-engaging portion of the acetabular inserter.

* * * * *